United States Patent
Cromwell

(10) Patent No.: US 10,646,686 B2
(45) Date of Patent: May 12, 2020

(54) DEVICE AND METHOD FOR AUDIO FREQUENCY THERAPY

(71) Applicant: Cymatics Technologies, Inc., Marietta, GA (US)

(72) Inventor: Mandara Dianne Cromwell, Marietta, GA (US)

(73) Assignee: Cymatics Technologies, Inc., Marietta, GA (US)

(*) Notice: Subject to any disclaimer, the term of this patent is extended or adjusted under 35 U.S.C. 154(b) by 0 days.

(21) Appl. No.: 15/837,419

(22) Filed: Dec. 11, 2017

(65) Prior Publication Data

US 2019/0175867 A1 Jun. 13, 2019

(51) Int. Cl.
*A61M 21/00* (2006.01)
*A61H 23/00* (2006.01)

(52) U.S. Cl.
CPC ............. *A61M 21/00* (2013.01); *A61H 23/00* (2013.01); *A61M 2021/0022* (2013.01); *A61M 2021/0027* (2013.01); *A61M 2205/502* (2013.01); *A61M 2205/8206* (2013.01)

(58) Field of Classification Search
CPC ........ A61H 23/00; A61H 23/008–0245; A61H 39/00–002; A61H 39/007; A61H 2201/5005
See application file for complete search history.

(56) References Cited

U.S. PATENT DOCUMENTS

| | | | |
|---|---|---|---|
| 4,708,127 A * | 11/1987 | Abdelghani | A61H 23/0245 310/319 |
| 5,876,135 A | 3/1999 | Wang et al. | |
| 6,143,946 A * | 11/2000 | Docter | A61F 13/0269 602/41 |
| 6,554,787 B1 * | 4/2003 | Griffin | A61F 7/02 601/70 |
| 7,424,325 B2 | 9/2008 | Koller et al. | |
| 8,041,430 B2 | 10/2011 | Lau | |
| 8,308,665 B2 | 11/2012 | Harry et al. | |
| 8,569,935 B1 | 10/2013 | Kosierkiewicz | |
| 9,205,249 B2 | 12/2015 | Pierenkemper | |
| 9,216,136 B2 * | 12/2015 | May | A61H 23/02 |
| 9,254,382 B2 | 2/2016 | Ahmad et al. | |
| 9,265,690 B2 | 2/2016 | Kriksunov et al. | |
| 9,308,363 B2 | 4/2016 | Goroszeniuk et al. | |
| 9,333,372 B2 | 5/2016 | Otis | |
| 9,403,000 B2 | 8/2016 | Lyons et al. | |

(Continued)

OTHER PUBLICATIONS

"AMI™ 750", Cyma Technologies, https://cymatechnologies.com/products/ami-750/, accessed on Nov. 13, 2017, website published in 2009.

*Primary Examiner* — Rachel T Sippel
(74) *Attorney, Agent, or Firm* — Thomas Horstemeyer, LLP

(57) ABSTRACT

Disclosed are various embodiments providing audio frequency therapy. An audio therapy device can emit vibrations of varying frequencies. When a controller of the device is activated, the controller can transmit frequency commutations to a transducer. The transducer can emit vibrations corresponding to the frequency commutations that cause at least a first enhancer and a second enhancer to vibrate. These vibrations are then transferred to one or more parts of a human body that are in contact with pads of the device.

20 Claims, 4 Drawing Sheets

(56) References Cited

U.S. PATENT DOCUMENTS

| | | |
|---|---|---|
| 9,457,166 B1 | 10/2016 | Lasorso, Jr. |
| 9,655,814 B2 | 5/2017 | Liu |
| 2004/0167446 A1* | 8/2004 | Podrazhansky ........ A61H 23/02 601/48 |
| 2006/0085047 A1 | 4/2006 | Unsworth et al. |
| 2006/0218692 A1* | 10/2006 | Lamarque .......... A41D 13/1245 2/114 |
| 2006/0224093 A1* | 10/2006 | Virag .................... A61F 5/0118 602/1 |
| 2007/0142891 A1 | 6/2007 | Stanley |
| 2007/0255187 A1* | 11/2007 | Branch .................... A61F 7/02 601/15 |
| 2008/0057320 A1 | 3/2008 | Komuro |
| 2009/0038179 A1 | 2/2009 | Chen |
| 2010/0249637 A1* | 9/2010 | Walter .................. A61H 23/02 600/544 |
| 2011/0064787 A1 | 3/2011 | Cabados |
| 2013/0296745 A1 | 11/2013 | Cheatham, II |
| 2013/0331907 A1 | 12/2013 | Sumners et al. |
| 2014/0018897 A1 | 1/2014 | Pastorelli |
| 2014/0180376 A1 | 6/2014 | Jennings |
| 2014/0209594 A1 | 7/2014 | Besner |
| 2015/0213724 A1 | 7/2015 | Shoshani |
| 2016/0213923 A1 | 7/2016 | Phillips |
| 2016/0310360 A1 | 10/2016 | Park |
| 2017/0157430 A1 | 6/2017 | Cheatham et al. |
| 2018/0092800 A1* | 4/2018 | Chapman ............... A61N 2/002 |

\* cited by examiner

DEVICE AND METHOD FOR AUDIO FREQUENCY THERAPY

BACKGROUND

Devices that provide therapy to the human body generally are based on infrared energy or electric stimulus. While these techniques are widely used, these devices cannot be used for long time durations as infrared energy or electric stimulus becomes difficult to bear after a certain time period.

BRIEF DESCRIPTION OF THE DRAWINGS

For a more complete understanding of the embodiments and the advantages thereof, reference is now made to the following description, in conjunction with the accompanying figures briefly described as follows.

Figure 1:
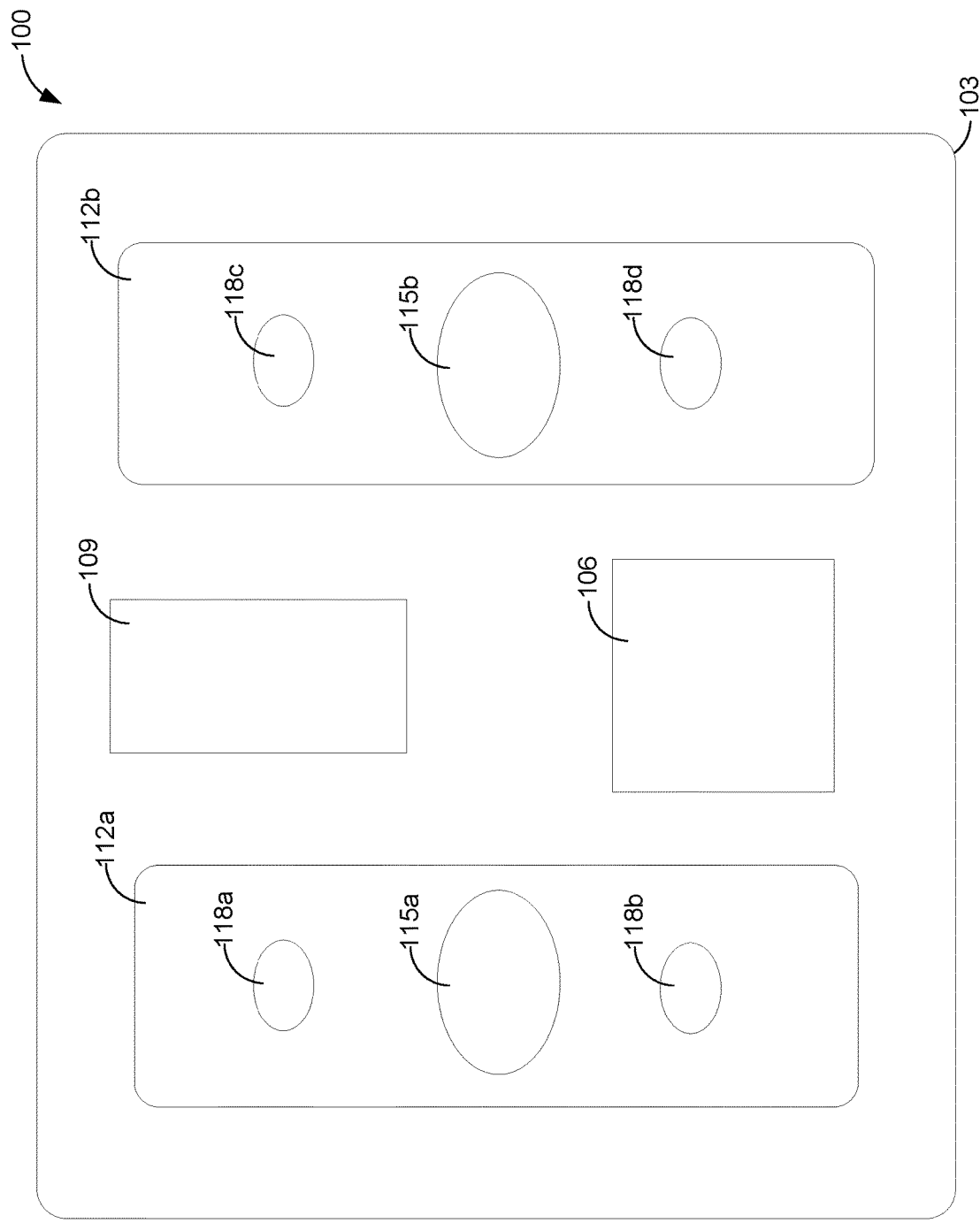
FIG. 1 is a schematic block diagram that illustrates a top view of a device for audio frequency therapy according to various example embodiments.

The drawings illustrate only example embodiments and are therefore not to be considered limiting of the scope described herein, as other equally effective embodiments are within the scope and spirit of this disclosure. The elements and features shown in the drawings are not necessarily drawn to scale, emphasis instead being placed upon clearly illustrating the principles of the embodiments. Additionally, certain dimensions may be exaggerated to help visually convey certain principles. In the drawings, similar reference numerals between figures designate like or corresponding, but not necessarily the same, elements.

DETAILED DESCRIPTION

In the following paragraphs, the embodiments are described in further detail by way of example with reference to the attached drawings. In the description, well known components, methods, and/or processing techniques are omitted or briefly described so as not to obscure the embodiments. As used herein, the "present disclosure" refers to any one of the embodiments of the disclosure described herein and any equivalents. Furthermore, reference to various feature(s) of the "present disclosure" is not to suggest that all embodiments must include the referenced feature(s).

Among embodiments, some aspects of the present disclosure are implemented by a computer program executed by one or more processors, as described and illustrated. As would be apparent to one having ordinary skill in the art, the present disclosure may be implemented, at least in part, by computer-readable instructions in various forms, and the present disclosure is not intended to be limiting to a particular set or sequence of instructions executed by the processor.

The embodiments described herein are not limited in application to the details set forth in the following description or illustrated in the drawings. The disclosure is capable of other embodiments and of being practiced or carried out in various ways. Also, the phraseology and terminology used herein is for the purpose of description and should not be regarded as limiting. The use of "including," "comprising," or "having" and variations thereof herein is meant to encompass the items listed thereafter, additional items, and equivalents thereof. The terms "connected" and "coupled" are used broadly and encompass both direct and indirect connections and couplings. In addition, the terms "connected" and "coupled" are not limited to electrical, physical, or mechanical connections or couplings. As used herein the terms "machine," "computer," "server," and "work station" are not limited to a device with a single processor, but may encompass multiple devices (e.g., computers) linked in a system, devices with multiple processors, special purpose devices, devices with various peripherals and input and output devices, software acting as a computer or server, and combinations of the above.

Research of cells in the human body has shown that cells communicate with other cells via sound waves. When a cell is receptive to a particular frequency, it will vibrate proportionally to the intensity of the signal and the vibrations may induce a biological response in the cell. The cell may also emit additional sound waves with unique characteristics. Various embodiments of the present disclosure are directed to transmitting particular vibrations to cells in the human body to provide therapeutic benefits.

Various embodiments of the present disclosure include a device and method of audio frequency therapy. One embodiment of a system, among others, includes a panel having a top surface and a bottom surface, at least one transducer affixed to the bottom surface of the panel, one or more gel pads affixed to the top surface of the panel, at least two first discs affixed to the panel in proximity to the at least two gel pads, at least two second discs affixed to the panel in proximity to the at least two gel pads, and a controller coupled to the transducer. The controller transmits to the transducer at least a first frequency commutation for a first time duration and a second frequency commutation for a second time duration. The first frequency commutation and second frequency commutation each include a set of at least two frequencies selected from a range of frequencies. These frequency commutations are emitted via the transducer and the vibrations corresponding to the frequencies in the frequency commutation travel via the panel, the at least two first discs, and the at least two second discs to vibrate at corresponding frequencies. When the gel pads are placed in contact with a human body, these vibrations are transferred to the human body and provide a therapeutic effect.

Figure 2:
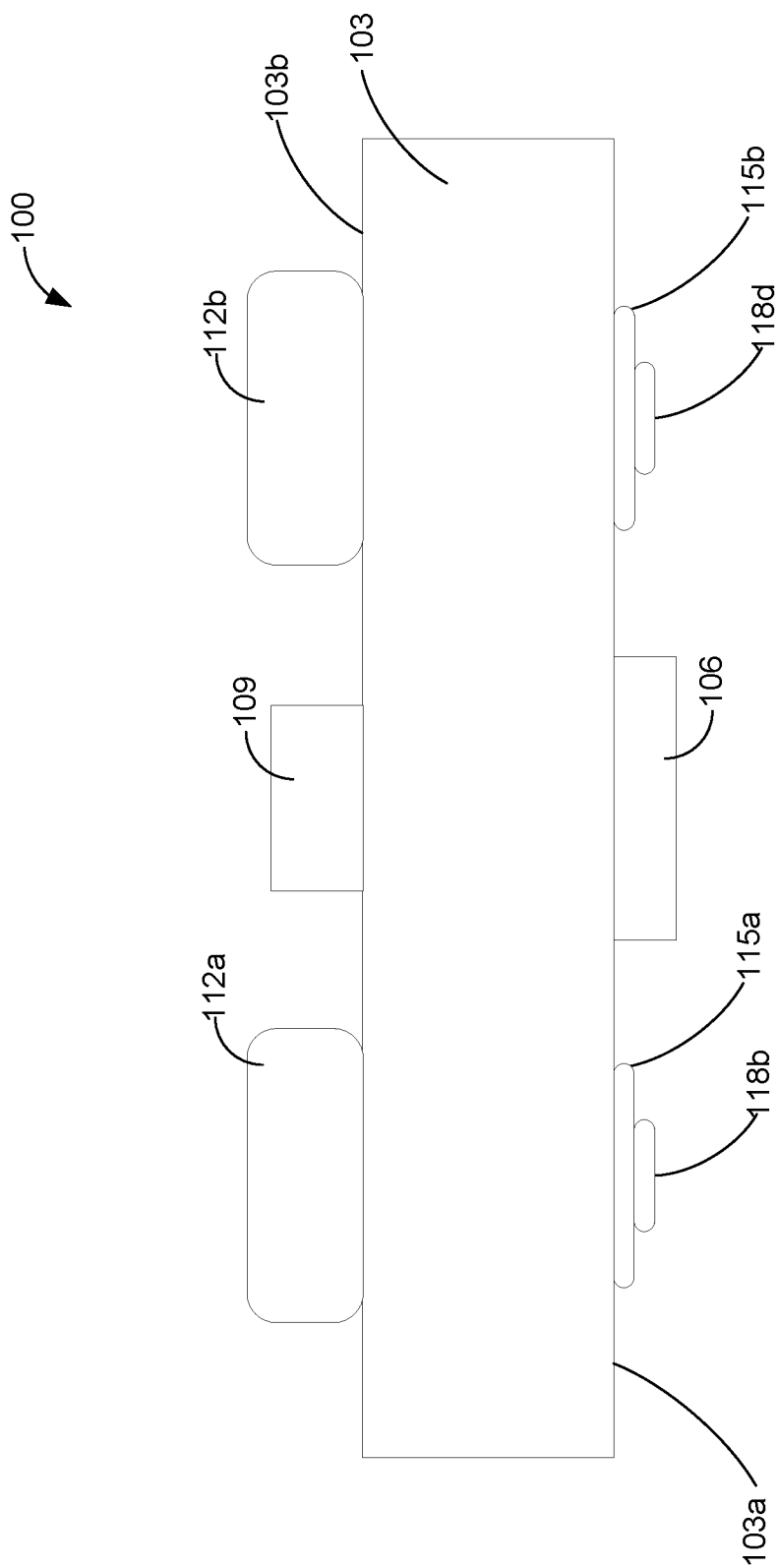
FIG. 2 is a schematic block diagram that illustrates a side view of the device of FIG. 1 for audio frequency therapy according to various example embodiments.

Turning now to the drawings, exemplary embodiments are described in detail. FIGS. 1 and 2 are schematic block diagrams that illustrate a Device 100 for audio frequency therapy according to various example embodiments. Device 100 includes Panel 103 having a bottom surface 103a and a top surface 103b. Affixed to Panel 103 are Transducer 106 and Controller 109. In various embodiments, Panel 103 is made of a plastic material that is conducive to carrying vibration with little or no dampening, such as, for example, a polycarbonate plastic resin. According to some embodiments, Panel 103 is generally flat and rectangular in shape. As will be appreciated, the shape and dimensions of panel 103 can be varied.

According to various embodiments, Transducer 106 is affixed to a bottom surface 103a of Panel 103, as depicted in FIG. 2. The Transducer 106 is electrically coupled to Controller 109. The Controller 109 can be affixed to either the top surface 103b or bottom surface 103a of Panel 103. The Transducer 106 and the Controller 109 can be affixed to Panel 103 by fasteners, such as, for example, screws, bolts, etc., or attached to the panel by a suitable adhesive, or removably attached such as, for example, with a velcro. In various embodiments, the Transducer 106 and the Controller 109 are combined in to a single part. In various embodiments, the Panel 103 may include housings configured to receive the Transducer 106 and/or the Controller 109 are affixed to the Panel 103 by placing them in the housings. For example, the Transducer 106 and/or the Controller 109 can be affixed via placement in a respective housing of the Panel 103, as can be appreciated.

The Controller 109 includes a processor, memory, and power source. The memory of the Controller 109 stores instructions that are executed by the processor to transmit one or more signals to the Transducer 106 that cause certain vibrations to be emitted via Transducer 106 for designated time periods. In various embodiments, the Controller 109 includes an interface to allow programming to be uploaded to the memory of Controller 109. Such an interface can be a wired interface, such as a USB port, an Ethernet port, a serial port, etc. Such an interface can also be wireless, such as a Bluetooth connection, WiFi connection, etc. The power source of the Controller 109 can be replaceable batteries, rechargeable batteries, or an interface to plug in to an AC or DC power source.

The Controller 109 may also include one or more input devices in the form of a control panel, one or more switches, buttons, touchscreen, etc., that enable a user of the Device 100 to control its operation. The input device allows the user to turn on the Device 100, select from one or more programs in the memory of the Device 100, begin a selected programmed cycle, etc. The programs in memory may include a number of preselected frequency commutations in a particular sequence. The input device may also allow the user to select individual frequencies, create a combination or commutation of frequencies from individually selected frequencies, retrieve a stored program in the device's memory, modify an existing program, etc. The Controller 109 may also include one or more output devices, such as a display device (LEDs, LCD display), an audio output device, etc. that provides information about the current state of operation of Device 100, as will be appreciated. Such an output device may also assist the user in programming the Controller 109 with custom frequency commutations.

Also included in Device 100 are pads 112. According to various embodiments, Pads 112 are water-based gel pads. In various embodiments, Pads 112 contain a mixture of distilled water and Carboxymethyl cellulose (CMC). The mixture is packaged in a plastic bag or pouch that is sealed to prevent leakage. In certain embodiments, the ratio of distilled water to CMC is about 97% to about 3%.

As shown in FIGS. 1 and 2, pads 112a and 112b can be rectangular in shape. Pads 112 are affixed to Panel 103 on the top surface 103b of Panel 103. According to various embodiments, the size of pads 112 can be larger than the size of an average human foot. In various embodiments, the size of each pad can be varied to be larger or smaller. In various embodiments, instead of one or two pads, there are a number of smaller (as compared to pads 112a and 112b) pads such that they cover the same or substantially the same surface area as each of two pads 112a and 112b. Pads 112 may be affixed to Panel 103 by an adhesive and/or tape. In various embodiments, the Pads 112 contain a lip surrounding the Pads 112. Threaded fasteners, such as screws, are used to retain the Pads 112 to Panel 103 by securely attaching Pads 112 to Panel 103 via holes in the lip. In various other embodiments, pads 112 are oval in shape. In various embodiments, pads 112 are configured to allow a foot to be placed on the pad. Pads 112 can also be made to contact other parts of the human body, such as hands, back, etc. For example, in various embodiments, there can be one large pad that covers a large portion (at least two thirds) of Panel 103, instead of 2 pads 112a and 112b.

The Device 100 includes First Enhancers 115, which are made from tourmaline, germanium, or a combination of tourmaline and germanium (where the ratio of tourmaline to germanium can vary from about 0% tourmaline to about 100% tourmaline and from about 100% germanium to about 0% germanium). In addition to tourmaline and/or germanium, the First Enhancers 115 may contain additional materials, such as fillers. In various embodiments, germanium and tourmaline may be compressed together to form one or more of the First Enhancers 115. In various embodiments, the First Enhancers 115 is made of tourmaline and or germanium crystals. In various embodiments, the First Enhancers 115 is generally in the shape of a disc.

First Enhancers 115a and 115b are located on Panel 103 on the bottom surface 103a of Panel 103. First Enhancers 115a and 115b may be affixed to panel by an adhesive. In various embodiments, First Enhancers 115a and 115b are located substantially at the center of pads 112a and 112b. In other embodiments, First Enhancers 115a and 115b are located such that they are in proximity to pads 112a and 112b respectively. For example, as shown in FIGS. 1 and 2, First Enhancers 115a is located on the bottom surface 103a of Panel 103 such that at least a part of its surface is covered by, or under at least a part of the surface of pad 112a. Similarly, First Enhancer 115b can be located in proximity to pad 112b such that at least a part of its surface is covered by at least a part of the surface of pad 112b.

In various embodiments, the First Enhancers 115 are located on the top surface 103b of Panel 103. In various embodiments, the First Enhancers 115 can be positioned in between the bottom surface 103a of Panel 103 and pad 112. In various embodiments, the First Enhancers 115 can be located inside pad 112. In various embodiments, the First Enhancers 115 can be located inside or embedded in Panel 103. In one non-limiting example, Panel 103 may be made of two separate sheets that are joined after placing the First Enhancers 115 in between the two sheets. In other embodiments, the First Enhancers 115 can be integrated within the panel using any other method of embedding or inserting the First Enhancers 115 in Panel 103, as can be appreciated. In various embodiments, First Enhancers 115 are generally in the shape of a disc.

The Device 100 also includes Second Enhancers 118. In various embodiments, Second Enhancers 118 are made from a crystal. In various embodiments, the crystal is a pure quartz crystal. Second Enhancers 118a-d are affixed to Panel 103 on the bottom surface 103a of Panel 103. Second Enhancers 118a-118d may be affixed to panel by an adhesive and/or tape. In various embodiments, Second Enhancers 118a and 118b are located substantially at the center of pads 112a, and Second Enhancers 118c and 118d are located substantially at the center of pads 112b. In various embodiments, Second Enhancers 118a and 118b are located such that they are in proximity to pad 112a, and Second Enhancers 118c and 118d are located such that they are in proximity to pad 112b. For example, as shown in FIGS. 1 and 2, Second Enhancers 118a and 118b are located in proximity to pad 112a such that at least a part of the surface of each of Second Enhancer 118a-b is covered by, or under, at least a part of the surface of pad 112a. Second Enhancers 118c and 118d are located in proximity to pad 112b such that at least a part the surface of each of Second Enhancers 118c-d is covered by at least a part of the surface of pad 112b.

In various embodiments, the Second Enhancers 118 are located on the top surface 103b of Panel 103. In various embodiments, the Second Enhancers 118 can be positioned in between the bottom surface 103a the Panel 103 and pad 112. In various embodiments, the Second Enhancers 118 can be located inside pad 112. In various embodiments, the Second Enhancers 118 can be located inside or embedded in Panel 103. In one non-limiting example, Panel 103 may be made of two separate sheets that are joined after placing Second Enhancers 118 in between the two sheets. In other embodiments, the Second Enhancers 118 can be integrated within the panel using any other method of embedding or inserting Second Enhancers 118 in Panel 103, as can be appreciated. In various embodiments, Second Enhancers 118 are generally in the shape of a disc.

Although the First Enhancer 115 and the Second Enhancer 118 are described as discs in various embodiments, one skilled in the art will recognize that the First Enhancers 115 and/or Second Enhancers 118 can be in any other shape without departing from the scope of the present disclosure. Further, the quantities and/or location of the first enhancer or the second Enhancer may be altered without departing from the scope of the present disclosure. Additionally, the size of the First Enhancers 115a and 115b and the Second Enhancers 118a, 118b, 118c, and 118d can be varied without departing from the scope of the disclosure. They can all be of different sizes, larger or smaller than the others.

Figure 3:
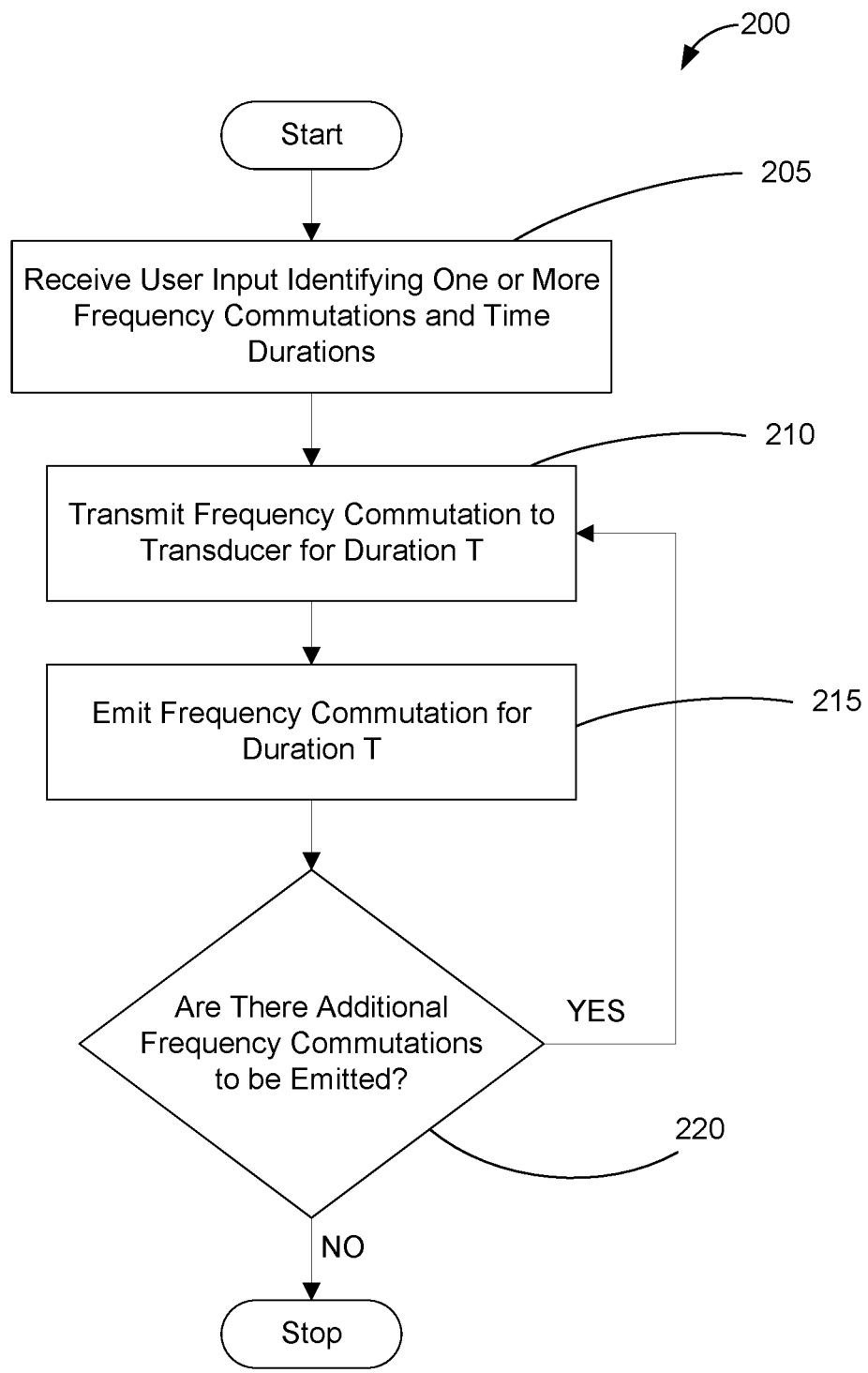
FIG. 3 illustrates an example flowchart of certain functionality implemented by portions of the device of FIGS. 1 and 2 for audio frequency therapy according to various embodiments of the present disclosure.

Before turning to the process flow diagrams of FIG. 3, it is noted that embodiments described herein may be practiced using an alternative order of the steps illustrated in FIG. 3. That is, the process flows illustrated in FIG. 3 are provided as examples only, and the embodiments may be practiced using process flows that differ from those illustrated. Additionally, it is noted that not all steps are required in every embodiment. In other words, one or more of the steps may be omitted or replaced, without departing from the spirit and scope of the embodiments. Further, steps may be performed in different orders, in parallel with one another, or omitted entirely, and/or certain additional steps may be performed without departing from the scope and spirit of the embodiments.

FIG. 3 illustrates an example flowchart of certain functionality implemented by portions of the Device 100 for audio frequency therapy according to various embodiments of the present disclosure. Process 200 begins when a user of Device 100 initiates one of one or more program sequences available in Device 100 via an input device of Controller 109, as depicted by block 205. The program sequence may include a number of frequency commutations and the time duration associated with each frequency commutation. In various embodiments, these frequency commutations and time durations may be pre-programmed and stored in the memory of Controller 109. In various other embodiments, the user may individually select or specify frequency commutations and time durations for each frequency commutation, via the input device coupled to Controller 109. In various other embodiments, the user may select or specify individual frequencies for each frequency commutation.

The Controller 109 then transmits a first frequency commutation in the sequence of frequency commutations to Transducer 106 for the associated time duration T, as depicted by block 210. The first frequency commutation includes multiple frequencies. In various embodiments, frequency commutation A includes at least five frequencies. Transducer 106 converts the signal transmitted by Controller 109 in to vibrations corresponding to the frequencies in the commutation, as depicted by block 215. These vibrations emitted via Transducer 106 travel through the First Enhancers 115, the Second Enhancers 118, the Panel 103, and the pads 112 causing these components to vibrate. These vibrations are then transferred to a portion of the human body in contact with pads 112.

After duration T associated with the first frequency commutation has elapsed, the process progresses to block 220. At block 220, Controller 109 determines if there is another frequency commutation in the program initiated by the user. If Controller 109 determines that there is another frequency commutation that is to be emitted, process returns to block 210 for the next frequency commutation to be transmitted, as described above in relation to blocks 210 and 215. If the Controller 109 determines that all the frequency commutations in the user selected program have been emitted, then the process 200 terminates.

In various embodiments, each frequency in the one or more frequency commutation is selected from the audible spectrum, e.g., about 20 Hz to about 20,000 Hz. In various embodiments, each frequency in the one or more frequency commutation is selected for a subset of the audible spectrum. In various embodiments, only a single frequency is used in a frequency commutation.

In various embodiments, each frequency in one or more commutations may be transmitted sequentially. In some embodiments, each frequency may be transmitted at equal durations. In other embodiments, the duration for each frequency may differ. For example, for one commutation including frequencies 1-5, the Controller 109 may transmit frequency 1 for a duration t1, frequency 2 for a duration of t2, frequency 3 for a duration t3, frequency 4 for a duration t4, and frequency 5 for a duration t5 to Transducer 106. In various such embodiments, each frequency in the commutation is only transmitted once. Alternatively, each frequency may be transmitted multiple times in the frequency commutation, e.g., by looping a sequence of frequencies.

In various other embodiments the frequencies in one or more commutation are transmitted simultaneously by Controller 109. During the duration of the commutation, all of the individual frequencies may be transmitted for the entire duration, or a portion of the duration. In one non-limiting example, one commutation consists of five frequencies, each frequency transmitted simultaneously for the duration of the commutation, e.g., five minutes. Each of the five frequencies in this non-limiting example is selected from a range between about 180 Hz and about 520 Hz. In one or more embodiments, a program may comprise multiple commutations, each commutation may have multiple frequencies, and transmitted (or played) for a duration, such as, about 3-10 minutes each.

Figure 4:
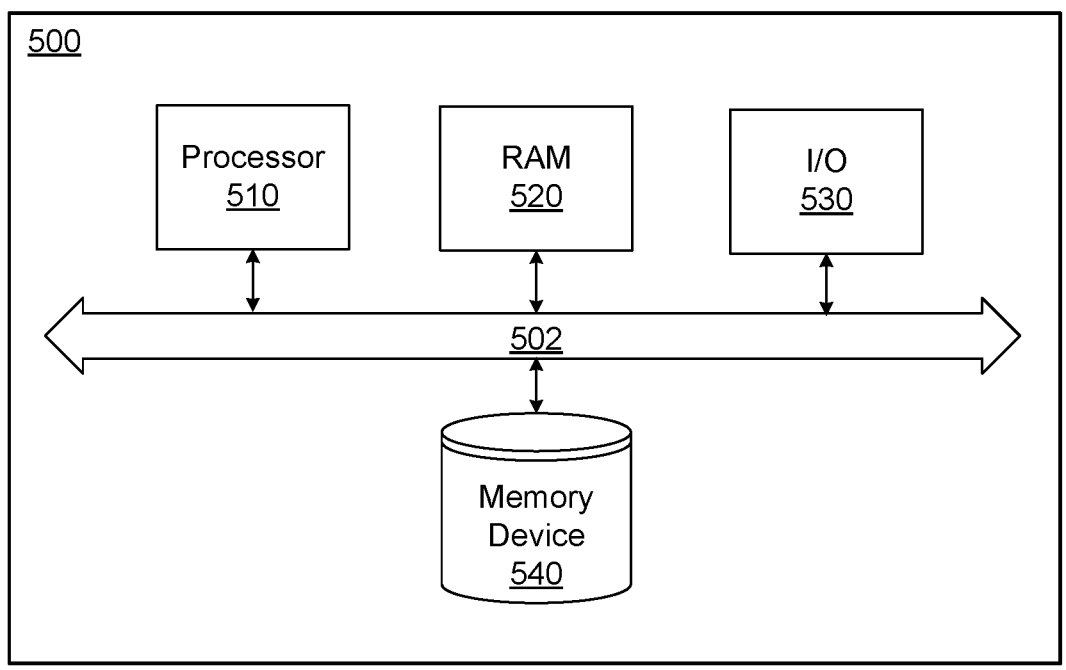
FIG. 4 is a schematic block diagram that illustrates an example controller of the device of FIG. 1 according to various embodiments.

Turning to FIG. 4, shown is a schematic block diagram that illustrates an example Controller 109 of Device 100 of FIG. 1 according to various embodiments. The Controller 500 includes a processor 510, a Random Access Memory ("RAM") 520, an Input Output ("I/O") interface 530, and a memory device 540. The elements of the Controller 500 are communicatively coupled via a bus 502.

The processor 510 comprises any well-known general purpose arithmetic processor or Application Specific Integrated Circuit ("ASIC"). The RAM 520 comprises any well known random access or read only memory device that stores computer-readable instructions to be executed by the processor 510. The memory device 540 stores computer-readable instructions thereon that, when executed by the processor 510, direct the processor 510 to execute various aspects of the present disclosure described herein. When the processor 510 comprises an ASIC, the processes described herein may be executed by the ASIC according to an embedded circuitry design of the ASIC, by firmware of the ASIC, or both an embedded circuitry design and firmware of the ASIC. As a non-limiting example group, the memory device 540 comprises one or more of an optical disc, a magnetic disc, a semiconductor memory (i.e., a semiconductor, floating gate, or similar flash based memory), a magnetic tape memory, a removable memory, combinations thereof, or any other known memory means for storing computer-readable instructions. The I/O interface 530 comprises device input and output interfaces such as keyboard, pointing device, display, communication, and other interfaces. The bus 502 electrically and communicatively couples the processor 510, the RAM 520, the memory device 540, and the I/O interface 560, so that data and instructions may be communicated among them.

In operation, the processor 510 is configured to retrieve computer-readable instructions stored on the memory device 540, the RAM 520, or another storage means (such as a ROM), and copy the computer-readable instructions to the RAM 520 for execution, for example. The processor 510 is further configured to execute the computer-readable instructions to implement various aspects and features of the present disclosure. For example, the processor 510 may be adapted and configured to execute the processes described above with reference to FIG. 3, including the processes described as being performed by the modules of the Controller 109. The I/O interface 530 further includes an amplifier, a digital to analog convertor, and/or other circuits to convert instructions from processor 510 to signals that can be transmitted to Transducer 106.

A phrase, such as "at least one of X, Y, or Z," unless specifically stated otherwise, is to be understood with the context as used in general to present that an item, term, etc., can be either X, Y, or Z, or any combination thereof (e.g., X, Y, and/or Z). Similarly, "at least one of X, Y, and Z," unless specifically stated otherwise, is to be understood to present that an item, term, etc., can be either X, Y, and Z, or any combination thereof (e.g., X, Y, and/or Z). Thus, as used herein, such phases are not generally intended to, and should not, imply that certain embodiments require at least one of either X, Y, or Z to be present, but not, for example, one X and one Y. Further, such phases should not imply that certain embodiments require each of at least one of X, at least one of Y, and at least one of Z to be present.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a range of "about 1 to about 5" should be interpreted to include not only the explicitly recited numerical value of about 1 to about 5, but also include individual numerical values (e.g., 1, 2, 3, and 4) and the sub-ranges (e.g., 0.5, 1.1, 2.2, 3.3, and 4.4) within the indicated range. The term "about" can include traditional rounding according to significant figures of numerical values. In addition, the phrase "about 'x' to 'y'" includes "about 'x' to about 'y'".

Although embodiments have been described herein in detail, the descriptions are by way of example. The features of the embodiments described herein are representative and, in alternative embodiments, certain features and elements may be added or omitted. Additionally, modifications to aspects of the embodiments described herein may be made by those skilled in the art without departing from the spirit and scope of the present disclosure defined in the following claims, the scope of which are to be accorded the broadest interpretation so as to encompass modifications and equivalent structures.

Therefore, at least the following is claimed:

1. A system, comprising:
   a panel having a top outer surface and a bottom outer surface;
   a transducer affixed to the bottom outer surface of the panel;
   at least two gel pads affixed to and in contact with the top outer surface of the panel, a first of the at least two gel pads being affixed to a first side of the top outer surface of the panel and a second of the at least two gel pads being affixed to a second side of the top outer surface of the panel opposite the first side;
   at least two first discs affixed to and in direct contact with the top outer surface of the panel, each of the at least two first discs being positioned under an outer surface of a respective one of the at least two gel pads and between the bottom outer surface and the respective one of the at least two gel pads, the at least two first discs being made from a first material, wherein a first of the at least two first discs is affixed to the first side of the top outer surface of the panel proximate to a center of the first of the at least two gel pads and a second of the at least two first discs is affixed to the second side of the top outer surface of the panel proximate to a center of the second of the at least two gel pads;
   at least two sets of second discs affixed to the top outer surface of the panel, each of the at least two sets of second discs being positioned under the outer surface of a respective one of the at least two gel pads, at least one of the at least two sets of second discs positioned adjacent to one of the at least two first discs, the at least two sets of second discs being made from a second material, and the first material being different from the second material, wherein:
      each of the at least two sets of second discs comprise two discs,
      a first of the at least two sets of second discs is affixed to the first side of the top outer surface of the panel and a second of the at least two sets of second discs is affixed to the second side of the top outer surface of the panel, and
      the first of the at least two first discs is positioned between respective discs of the first of the at least two sets of second discs and the second of the at least two first discs is positioned between respective discs of the second of the at least two sets of second discs;
   a controller affixed to the top outer surface of the panel and coupled to the transducer, the controller being positioned between the first of the at least two gel pads and the second of the at least two gel pads; and
   an input device coupled to the controller, the input device being configured to receive an input corresponding to a sequence of frequency commutations, wherein, in response to the input being received by the input device, the controller causes the transducer to at least emit a first vibration corresponding to a first frequency commutation of the sequence of frequency commutations for a first time duration and emit a second vibration corresponding to a second frequency commutation of the sequence of frequency commutations for a second time duration, the first frequency commutation and the second frequency commutation each comprising at least two different discrete frequencies selected from a range of frequencies in an audible spectrum, and the first time duration being different from the second time duration.

2. The system of claim 1, wherein the first vibration and the second vibration cause the panel, the at least two first discs, and the at least two sets of second discs to vibrate at corresponding frequencies.

3. The system of claim 1, wherein the second material is made from at least one of: tourmaline, germanium, or a combination of tourmaline and germanium.

4. The system of claim 1, wherein at least a portion of the at least two first discs and at least a portion of the at least two sets of second discs are embedded in the top outer surface of the panel.

5. A device, comprising:
a panel having a top outer surface and a bottom outer surface;
a transducer affixed to the bottom outer surface of the panel;
at least two gel pads affixed to and in contact with the top outer surface of the panel, a first of the at least two gel pads being affixed to a first side of the top outer surface of the panel and a second of the at least two gel pads being affixed to a second side of the top outer surface of the panel opposite the first side;
at least two first enhancers affixed to and in direct contact with the top outer surface of the panel, each of the at least two first enhancers being positioned under an outer surface of a respective one of the at least two gel pads and between the bottom outer surface and the respective one of the at least two gel pads, the at least two first enhancers being made from a first material, wherein a first of the at least two first enhancers is affixed to the first side of the top outer surface of the panel proximate to a center of the first of the at least two gel pads and a second of the at least two first enhancers is affixed to the second side the top outer surface of the panel proximate to a center of the second of the at least two gel pads;
at least two sets of second enhancers affixed to the top outer surface of the panel, each of the at least two sets of second enhancers being positioned under an outer surface of a respective one of the at least two gel pads, at least one of the at least two sets of second enhancers positioned adjacent to one of the at least two first enhancers, the at least two sets of second enhancers being made from a second material, and the first material being different from the second material, wherein:
each of the at least two sets of second enhancers comprise two enhancers,
a first of the at least two sets of second enhancers is affixed to the first side of the top outer surface of the panel and a second of the at least two sets of second enhancers is affixed to the second side of the top outer surface of the panel, and
the first of the at least two first enhancers is positioned between respective enhancers of the first of the at least two sets of second enhancers and the second of the at least two first enhancers is positioned between respective enhancers of the second of the at least two sets of second enhancers;
a controller affixed to the top outer surface of the panel and coupled to the transducer, the controller being positioned between the first of the at least two gel pads and the second of the at least two gel pads; and
an input device coupled to the controller, the input device being configured to receive an input corresponding to a sequence of frequency commutations, wherein, in response to the input being received by the input device, the controller causes the transducer to at least emit a first vibration corresponding to a first frequency commutation of the sequence of frequency commutations for a first time duration and emit a second vibration corresponding to a second frequency commutation of the sequence of frequency commutations for a second time duration, the first frequency commutation and the second frequency commutation each comprising at least two different discrete frequencies selected from a range of frequencies in an audible spectrum, and the first time duration being different from the second time duration.

6. The device of claim 5, wherein the at least two gel pads comprise two or more water-based gel pads.

7. The device of claim 6, wherein each of the two or more water-based gel pads is in contact with the top outer surface of the panel.

8. The device of claim 5, wherein the first material is made from at least one of tourmaline, germanium, or a combination of tourmaline and germanium.

9. The device of claim 5, wherein the at least two first enhancers and the at least two sets of second enhancers are shaped as discs.

10. The device of claim 5, wherein:
the first of the at least two first enhancers is affixed to the top outer surface of the panel at a first location; and
the second of the at least two first enhancers is affixed to the top outer surface of the panel at a second location.

11. The device of claim 10, wherein:
the first location is in proximity to a location of the first of the at least two gel pads; and
the second location is in proximity to a location of the second of the at least two gel pads.

12. The device of claim 5, wherein the at least two sets of second enhancers are crystals.

13. The device of claim 5, wherein:
the first of the at least two sets of second enhancers is affixed to the top outer surface of the panel at least at a first location; and
the second of the at least two sets of second enhancers is affixed to the top outer surface of the panel at a second location.

14. The device of claim 13, wherein:
the first location is in proximity to a location of the first of the at least two gel pads; and
the second location is in proximity to a location of the second of the at least two gel pads.

15. A method for audio frequency therapy, comprising:
receiving, via a controller affixed to a top outer surface of a panel, user input identifying a sequence of frequency commutations and a plurality of respective time durations;
transmitting, via the controller, a first frequency commutation of the sequence of frequency commutations to a transducer affixed to a bottom outer surface of the panel and controlled by the controller for a first time duration of the plurality of respective time durations in response to receiving the user input, the first frequency commutation comprising at least two different and discrete frequencies selected from a range of frequencies in an audible spectrum;

emitting, by the transducer controlled by the controller, a first vibration corresponding to the first frequency commutation for the first time duration;

transmitting, via the controller, a second frequency commutation of the sequence of frequency commutations to the transducer for a second time duration of the plurality of respective time durations, the second frequency commutation comprising at least two other different and discrete frequencies selected from the range of frequencies in the audible spectrum, and the second time duration being different from the first time duration; and emitting, by the transducer controlled by the controller, a second vibration corresponding to the second frequency commutation for the second time duration, wherein the first vibration and the second vibration cause at least:

the panel, at least two gel pads affixed to and in contact with the top outer surface of the panel, a first of the at least two gel pads being affixed to a first side of the top outer surface of the panel and a second of the at least two gel pads being affixed to a second side of the top outer surface of the panel opposite the first side, at least two first enhancers affixed to and in direct contact with the top outer surface of the panel and positioned under an outer surface of a respective one of the at least two gel pads and between the bottom outer surface of the panel and the respective one of the at least two gel pads, and at least two sets of second enhancers affixed to the top outer surface of the panel and positioned under an outer surface of a respective one of the at least two gel pads to vibrate at one or more frequencies that correspond to the at least two different and discrete frequencies in the first frequency commutation and the at least two other different and discrete frequencies in the second frequency commutation, the at least two first enhancers comprising a first material, and the at least two sets of second enhancers comprising a second material that is different from the first material, wherein:

at least one of the at least two sets of second enhancers is positioned adjacent to one of the at least two first enhancers, a first of the at least two first enhancers is affixed to the first side of the top outer surface of the panel proximate to a center of the first of the at least two gel pads and a second of the at least two first enhancers is affixed to the second side of the top outer surface of the panel proximate to a center of the second of the at least two gel pads, and the first of the at least two first enhancers is positioned between respective enhancers of the first of the at least two sets of second enhancers and the second of the at least two first enhancers is positioned between respective enhancers of the second of the at least two sets of second enhancers;

the controller is positioned between the first of the at least two gel pads and the second of the at least two gel pads.

16. The method of claim 15, wherein the controller transmits a plurality of electrical signals that cause the transducer to emit the first vibration and the second vibration.

17. The method of claim 15, wherein at least one of: the first vibration or the second vibration is transferred to a part of a human body in contact with the at least one pad two gel pads.

18. The method of claim 15, wherein:

the sequence of frequency commutations is selected from a plurality of preprogrammed frequency commutations; and the plurality of respective time durations is selected from a plurality of preprogrammed time durations.

19. The method of claim 15, wherein:

each of the sequence of frequency commutations comprises individual frequencies that are specified by a user; and the plurality of respective time durations is specified by the user.

20. The method of claim 15, further comprising:

determining, via the controller, that the sequence of frequency commutations further comprises a third frequency commutation;

transmitting, via the controller, the third frequency commutation to the transducer for a third time duration of the plurality of respective time durations; and emitting, by the transducer controlled by the controller, a third vibration corresponding to the third frequency commutation for the third time duration.

* * * * *